United States Patent
Helsing

(10) Patent No.: US 11,000,050 B2
(45) Date of Patent: May 11, 2021

(54) **BIRD FEED AND IN PARTICULAR POULTRY FEED, COMPRISING SYNTHETIC CAPSAICINOID DERIVATIVES AND SUCH FEED FOR PROPHYLACTIC USE OR TREATMENT OF *SALMONELLA* INFECTION**

(71) Applicant: aXichem AB, Bergen (NO)

(72) Inventor: Torsten Helsing, Kleppestø (NO)

(73) Assignee: AXICHEM AB, Malmo (SE)

( * ) Notice: Subject to any disclaimer, the term of this patent is extended or adjusted under 35 U.S.C. 154(b) by 0 days.

(21) Appl. No.: 15/766,924

(22) PCT Filed: Oct. 9, 2015

(86) PCT No.: PCT/NO2015/050186
§ 371 (c)(1),
(2) Date: Apr. 9, 2018

(87) PCT Pub. No.: WO2017/061871
PCT Pub. Date: Apr. 13, 2017

(65) Prior Publication Data
US 2019/0059417 A1    Feb. 28, 2019

(51) Int. Cl.
*A23K 50/70* (2016.01)
*A23K 20/111* (2016.01)
*A23K 50/75* (2016.01)

(52) U.S. Cl.
CPC ............ *A23K 20/111* (2016.05); *A23K 50/70* (2016.05); *A23K 50/75* (2016.05); *A23V 2002/00* (2013.01)

(58) Field of Classification Search
None
See application file for complete search history.

(56) References Cited

U.S. PATENT DOCUMENTS

| 4,532,139 A | 7/1985 | Janusz et al. |
| 5,821,269 A * | 10/1998 | Blumberg ............ A23K 20/111 424/760 |
| 2007/0148146 A1 | 6/2007 | Doyle et al. |
| 2007/0167524 A1* | 7/2007 | Helsing ................. A01N 37/18 514/627 |
| 2010/0055253 A1 | 3/2010 | Gautier et al. |
| 2013/0136695 A1 | 5/2013 | Hargis et al. |

FOREIGN PATENT DOCUMENTS

| CN | 101999541 | 4/2011 |
| CN | 102318754 | 1/2012 |
| CN | 102550870 | 7/2012 |
| CN | 104664173 | 6/2015 |
| EP | 1 670 310 | 6/2006 |
| FR | 2 908 600 | 5/2008 |

(Continued)

OTHER PUBLICATIONS

International Search Report dated Jan. 26, 2016 in International (PCT) Application No. PCT/NO2015/050186.

(Continued)

*Primary Examiner* — Sudhakar Katakam
*Assistant Examiner* — Jennifer C Sawyer
(74) *Attorney, Agent, or Firm* — Wenderoth, Lind & Ponack, L.L.P.

(57) ABSTRACT

The invention relates to bird feed comprising synthetic capsaicinoids for prohylactic use or treatment of *salmonella* infection.

4 Claims, 1 Drawing Sheet

Rank number of CFU/g values of control (round dots) and the 20 mg/kg phenylcapsaicin treatment (triangular dots) (x-axis) plotted against CFU/g counts (y-axis) on day 20 (a) and day 29 (b)

(56) References Cited

FOREIGN PATENT DOCUMENTS

| | | |
|---|---|---|
| GB | 2492318 | 1/2013 |
| JP | 1-172330 | 7/1989 |
| JP | 10-509307 | 9/1998 |
| JP | 2002-515229 | 5/2002 |
| JP | 2002-193821 | 7/2002 |
| JP | 2002-325541 | 11/2002 |
| JP | 2007-505104 | 3/2007 |
| JP | 2008-537550 | 9/2008 |
| JP | 2013-151442 | 8/2013 |
| KR | 2001-0099502 | 11/2001 |
| WO | 92/03923 | 3/1992 |
| WO | 99/59430 | 11/1999 |
| WO | 2006/107723 | 10/2006 |
| WO | 2010/014038 | 2/2010 |
| WO | 2013/071298 | 5/2013 |
| WO | 2015/160842 | 10/2015 |

OTHER PUBLICATIONS

International Preliminary Report on Patentability dated Jan. 10, 2018 in International (PCT) Application No. PCT/NO2015/050186.
Written Opinion of the International Searching Authority dated Apr. 13, 2017 in International (PCT) Application No. PCT/NO2015/050186.
Examination Report dated Mar. 8, 2019 in Australian Patent Application No. 2015411375.
Tellez G. I. et al., "Effect of prolonged administration of dietary capsaicin on *Salmonella enteritidis* infection in leghorn chicks", *Avian Diseases*, vol. 37, No. 1 (Jan.-Mar. 1993), pp. 143-148.
McElroy A.P. et al., "Effect of prolonged administration of dietary capsaicin on broiler growth and *Salmonella enteritidis* susceptibility", *Avian Diseases*, vol. 38, No. 2 (Apr.-Jun. 1994), pp. 329-333.
Negulesco J. A. et al., "Effects of pure capsaicinoids (capsaicin and dihydrocapsaicin) on plasma lipid and lipoprotein concentrations of turkey poults", *Atherosclerosis*, vol. 64, No. 2/3, Apr. 1, 1987, pp. 85-90.

\* cited by examiner

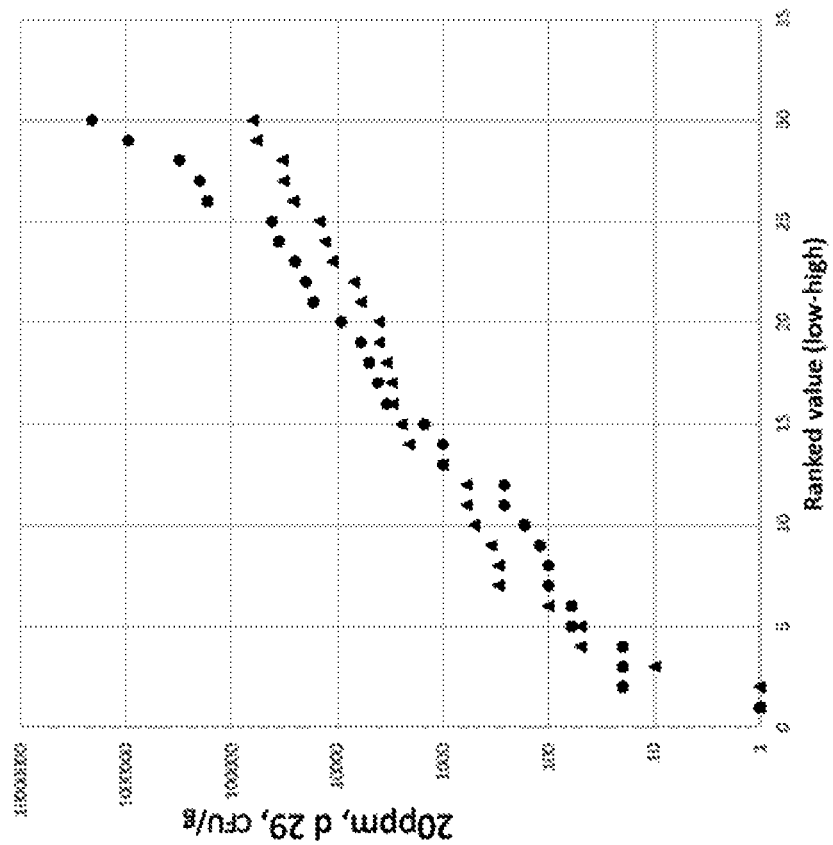
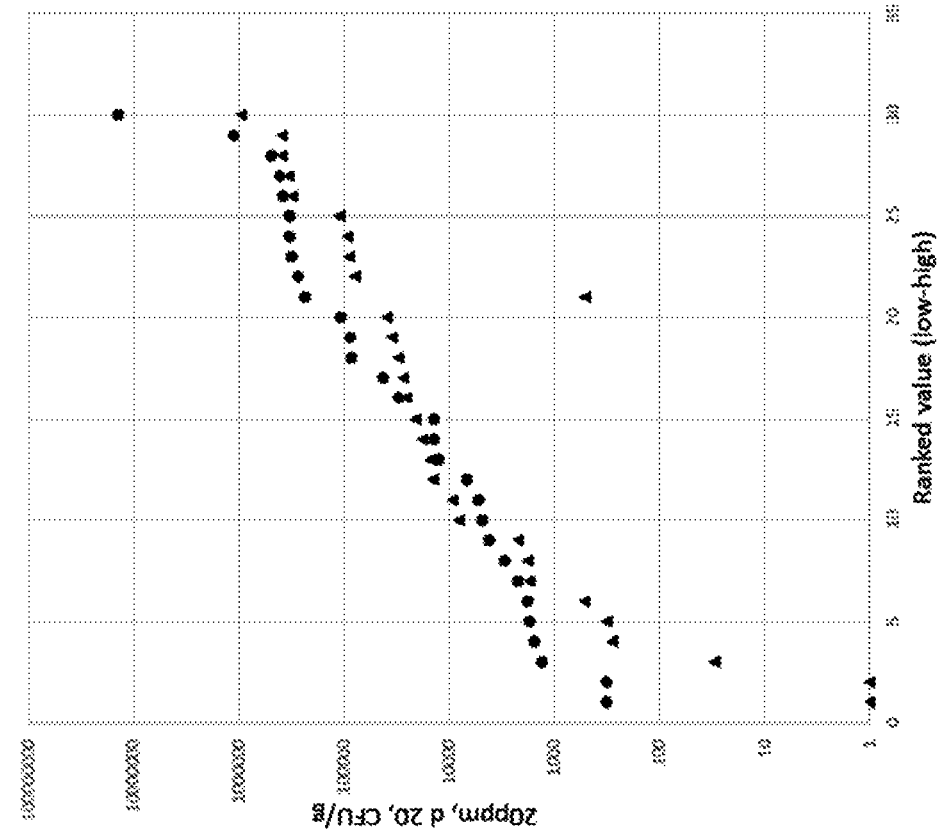
Rank number of CFU/g values of control (round dots) and the 20 mg/kg phenylcapsaicin treatment (triangular dots) (x-axis) plotted against CFU/g counts (y-axis) on day 20 (a) and day 29 (b)

BIRD FEED AND IN PARTICULAR POULTRY FEED, COMPRISING SYNTHETIC CAPSAICINOID DERIVATIVES AND SUCH FEED FOR PROPHYLACTIC USE OR TREATMENT OF *SALMONELLA* INFECTION

FIELD OF THE INVENTION AND RELATED PRIOR ART

The invention relates to bird feed and in particular poultry feed comprising synthetic capsaicinoid derivatives and such feed for prohylactic use or treatment of *salmonella* infection in broiler chickens.

aXichem is a global supplier of natural-analogue industrial compounds and its mission is to develop, patent and market natural-analogue substances. aXichem is focusing on phenylcapsaicin, an analogue of natural capsaicin and derivatives thereof. Since phenylcapsaicin is synthetically produced, the substance offers a wide range of benefits compared with natural capsaicin, which is extracted from chili peppers and therefore has a varying quality. Synthetic capsaicinoids can be prepared with high purity and in good yields and quantity and at a reasonable cost. Additionally, the available amounts of naturally occurring capsaicin is limited. The standardized natural capsaicin extract contains at least 3 isomers, which all have different chemical properties but which are difficult to differentiate between. It may therefore be difficult to obtain capsaicin extracts which have sufficiently uniform purity and composition for the intended use.

Phenylcapsaicin is not environmentally harmful and is thus a viable alternative with a wide range of applications in a variety of areas. aXichem holds European (EP1670310) and US patents (U.S. Pat. No. 7,446,226) on their synthetic products their synthesis and use as antifouling agent (WO2005025314).

Intestinal colonisation of *Salmonella* bacteria in poultry is a major concern for food safety in humans. *Salmonella* shedding within a flock occurs via *Salmonella* excretion in faeces. Crhanova M, et. al.: Immune response of chicken gut to natural colonization by gut microflora and to *Salmonella enterica* serovar *enteritidis* infection. *Infect Immun* 2011, 79(7):2755-2763.

In relation to food safety, control of *Salmonella* during the production of animal products is an important issue. Poultry constitute a reservoir of *Salmonella* and numerous outbreaks of salmonellosis are associated with the consumption of poultry products. *Salmonella* is able to colonise in the crop and the intestinal tract of poultry. In order to reduce the *Salmonella* problems in relation to food safety, there is an increasing interest to reduce colonisation of *Salmonella* in the digestive tract of poultry and shedding of *Salmonella* via excreta by modifications of the diet or by drinking water supplementations.

*Salmonella* infected poultry in addition to direct food poisoning cause contamination during transport and storage, in slaughter houses, in restaurants, kitchens and grocery stores. Decontamination is very costly and there is a large benefit if avoided.

*Salmonella* infection represents a serious problem for the global poultry industry. Infection leads to large economic losses for the whole industry, and also causes a range of other negative consequences.

Currently, three different technologies are used to combat *salmonella* infection: antibiotics, addition of organic acids (primarily lactic acid) to drinking water and enzymatic treatments. A range of problems are associated with all these treatments; primarily development of antibiotic resistance, which is a serious problem, secondly, enzyme and acid treatments are found to have highly limited effects. It can also be noted that lactic acid treatment can cause corrosion problems in drinking water systems, and also affect the birds' feed uptake and general quality.

SUMMARY OF THE INVENTION

The present application relates to bird feed comprising at least one chemical compound with the general formula (I) in claim 1 wherein R is a substituent selected from the group of $C_1$-$C_{18}$ alkyl, trifluoromethyl, $C_3$-$C_{12}$ cycloalkyl, phenyl, phenoxy, phenylthio, halogen; or tautomers or salts thereof.

Specifically synthetic capsaicinoids in this application relates to alkyn derivatives wherein the R group is as defined in claim 1.

The application also relates to bird feed as defined above for prophylactic or therapeutic use for resistance to or treatment of *salmonella* infection in birds.

DETAILED DESCRIPTION OF THE INVENTION

The present application relates to bird feed comprising at least one chemical compound with the general formula (I) in claim 1 wherein R is a substituent selected from the group of $C_1$-$C_{18}$ alkyl, trifluoromethyl, $C_3$-$C_{12}$ cycloalkyl, phenyl, phenoxy, phenylthio, halogen; or tautomers or salts thereof.

Preferably the bird feed according to claim 1, comprises phenylcapsaicin.

Preferably the bird feed comprises 5-40 mg/kg of a compound of formula I, even more preferably 20 mg/kg.

The application also relates to bird feed as defined above for prophylactic or therapeutic use for resistance to or treatment of *salmonella* infection in birds.

The birds are selected from the group consisting of from poultry, in particular broiler chicken; egg producing birds, in particular chickens; turkey; ostrich; quail; grouse; ducks; geese; wild birds; tame birds and breeding birds.

The feed is selected from one or more of the group consisting of seeds, corn, worms, millet, oat, peanuts and in the form of pellets, slurry, drinking water and emulsions.

The *salmonella* infection is selected from the group caused by *Salmonella* Mongori; *Salmonella* Hadar; Salmonelle Montevideo; *Salmonella* Epinay and *Salmonella Enterica* from the subspecies *enterica, salamae, arizonae, diazonae, houtenase* and *indica.*

Preferably the *salmonella* infection is caused by *Salmonella enteritidis*, in particular *Salmonella enteritidis* PT4.

Phenylcapsaicin offers a prophylactic treatment of *salmonella* and the spread of *salmonella* in poultry production units. The basic principle is simple: phenylcapsaicin—after formula 1—is added in small quantities, typically 5-20 ppm, to the bird feed or the birds' drinking water. This results in a reduced occurrence of *salmonella* in the individual bird's digestive system, and thus also a reduced spread of infection between the birds via faeces.

The exact mechanism of action is still not known. However, it is believed that the mechanism could be that phenylcapssaicin has a direct antibacterial effect in the birds exposed to the invention, and thus reduces bacterial growth directly. This mechanism is currently under investigation.

The other proposed mechanism of action is that phenylcapsaicin contributes to change the birds' microbiota in a favorable way. This proposed explanation means that the *salmonella* infection is fought indirectly in the bird, as the phenylcapsaicin affects endogenous, microbiotic processes, and thereby reduces the number of *salmonella* bacteria in the birds' digestive system.

The reduced number of *salmonella* bacteria in the digestive system naturally leads to reduced excretion of bacteria in faeces, which is the primary contamination pathway between the birds.

Thus, feeding of production birds with phenylcapsaicin enriched feed will counter the spread of *salmonella* in individual birds as well as prevent infection between the birds.

Another use of capsaicin related compounds is as rodent (mammal) repelling agents in outdoor feeding of birds and other animals. Synthetic derivatives produced in high purity and high quantity and to a reasonable cost will be superior to extracts from peppers in this use.

Synthetic capsaicinoids are well-suited to a variety of applications, including marine antifouling paint, pest control in forestry and agriculture and certain pharmaceutical applications. Phenylcapsaicin has also demonstrated potential properties as an anti-microbial and growth promoter in feed for commercial poultry production.

FIGURES

FIG. 1—Rank number of CFU/g values of control (blue dots) and the 20 mg/kg phenylcapsaicin treatment (red dots) (x-axis) plotted against CFU/g counts (y-axis) on day 20 (a) and day 29 (b)

EXPERIMENTAL

An experiment in which the effect of phenylcapsaicin, supplemented at different dose levels to broiler feed, against *Salmonella* colonisation and translocation has been conducted. Besides the effect against *Salmonella* infection the effect of phenylcapsaicin on growth performance was studied.

The study aimed to evaluate the effects of dietary inclusion at different dose levels of phenylcapsaicin, an analogue of natural capsaicin (1% solution in soy oil) on the intestinal colonisation and translocation of *Salmonella enteritidis* and growth performance of *Salmonella* challenged broilers. The experiment was carried out with 420 Ross 308 male broilers and lasted 30 days. The birds were housed in thirty three-tier battery cages (14 birds per cage at the start).

Five experimental treatments were evaluated, each replicated six times. The experimental design is outlined in Table 1. Treatment I consisted of birds which were not challenged with *Salmonella enteritidis* and received the control diet. The birds of treatments II, III, IV and V were all challenged with *Salmonella enteritidis* PT4 and received a control diet or the control diet with 20 mg/kg, 28 mg/kg or 36 mg/kg phenylcapsaicin, respectively. The control diet used is found in Table 2.

TABLE 1

Experimental design - *Salmonella* challenged broiles.

| Group | Number of cages | Dietary treatment | *Salmonella enteritidis* challenge |
|---|---|---|---|
| I | 6 | None (Control diet) | No |
| II | 6 | None (Control diet) | Yes |

TABLE 1-continued

Experimental design - *Salmonella* challenged broiles.

| Group | Number of cages | Dietary treatment | *Salmonella enteritidis* challenge |
|---|---|---|---|
| III | 6 | 20 mg/kg phenylcapsaicin | Yes |
| IV | 6 | 28 mg/kg phenylcapsaicin | Yes |
| V | 6 | 36 mg/kg phenylcapsaicin | Yes |

TABLE 2

Control diet used - Salmonelle challenged broiles

| | | Starter 0-15 days | Grower 15-30 days |
|---|---|---|---|
| Maize | g/kg | 317.6 | 191.3 |
| Wheat | g/kg | 250.0 | 400.0 |
| Soybean meal CP 480 g/kg | g/kg | 280.0 | 260.0 |
| Rape seed meal CP 335 g/kg | g/kg | 50.0 | 50.0 |
| Potato protein Ash >10 g/kg | g/kg | 10.0 | 0.0 |
| Soy oil | g/kg | 52.0 | 65.0 |
| Premix | g/kg | 5.0 | 5.0 |
| Lime | g/kg | 16.0 | 14.0 |
| Monocalciumphosphate | g/kg | 9.5 | 5.5 |
| Salt | g/kg | 2.0 | 2.1 |
| Sodiumbicarbonate | g/kg | 3.0 | 2.5 |
| Natuphos 10000G (phytase - enzyme) | g/kg | 0.05 | 0.05 |
| Hostazym NSP-enzyme | g/kg | 0.10 | 0.10 |
| Clinacox | g/kg | 0.20 | 0.20 |
| L-lysine HCl | g/kg | 1.75 | 1.75 |
| DL-methionine | g/kg | 2.20 | 1.85 |
| L-threonine | g/kg | 0.45 | 0.50 |
| L-valine | g/kg | 0.15 | 0.15 |
| Total | g/kg | 1000.0 | 1000.0 |
| Calculated nutrients (g/kg) | | | |
| Crude protein | g/kg | 218 | 207 |
| Crude fat | g/kg | 74 | 83 |
| Crude fibre | g/kg | 29 | 29 |
| Ash | g/kg | 61 | 54 |
| Dig. Lysine | g/kg | 10.7 | 10.4 |
| Dig. Methionine | g/kg | 5.0 | 4.6 |
| dig M + C | g/kg | 8.0 | 7.6 |
| Dig. Threonine | g/kg | 6.9 | 6.7 |
| Dig. Valine | g/kg | 8.5 | 8.3 |
| $ME_{broiler}$[1] | MJ/kg | 12.07 | 12.43 |
| Ca | g/kg | 9.4 | 8.0 |
| P total | g/kg | 6.0 | 5.1 |
| Av. P | g/kg | 4.0 | 3.3 |
| Na | g/kg | 1.7 | 1.6 |
| Cl | g/kg | 2.0 | 2.1 |
| K | g/kg | 8.9 | 8.5 |

The broilers were inoculated in the crop on days 15 and 16 of age with on average $3.7 \times 10^8$ CFU nalidixic acid resistant *Salmonella enteritidis* PT4. Based on necropsy of five birds per cage on days 20 and 29 of age, *Salmonella enteritidis* counts in the caecal digesta (intestinal colonization) and spleen (translocation) were determined. Growth performance of the birds (body weight gain, feed intake and feed conversion ratio) was determined at 15 and 30 days of age.

Measurements
Test Product
The soy oil with the 1% solution of phenylcapsaicin was analysed for the phenylcapsaicin dose.
Experimental Diets
Samples of each experimental diet (4 starter and 4 grower diets) were analysis on the inclusion level of phenyl capsaicin.

Samples of each experimental diet (4 starter and 4 grower diets) were analysed for dry matter, ash, crude protein, crude fat (HCL), crude fibre, calcium and phosphorus.

Droppings

At 13 days of age (prior to inoculation) droppings were sampled and pooled per cage to determine the initial *Salmonella enteritidis* situation. Droppings per cage were collected over a period of 2 h on clean paper underneath each cage.

Caecal Digesta and Spleen Sampling

*Salmonella enteritidis* concentration in digesta of the caeca and of the spleen were measured to determine intestinal colonization and translocation, respectively, by sacrificing five random birds per cage on 20/21 and 29/30 days of age. For this purpose the birds were euthanized. During inoculation at day 15/16, in each pen five randomly chosen birds were marked with a green wingtag and five randomly chosen birds were marked with a blue wingtag. At 20/21 days the birds with a green wingtag were sacrificed and at 29/30 days of age the birds with the blue wingtag were euthanized. Birds were first anaesthetized by a mixture of Sedamun and Ketamine (5:3) via injection in the breast muscle (dosage: 1 ml/kg BW) and subsequently euthanized by an intravenous injection of T61 (an aqueous solution containing (in mg per ml) embutramide, 200; mebezoniumiodide, 50; tetracainehydrochloride, 5). After euthanizing the birds were weighed and thereafter the caecal digesta and the spleen were collected. After collection, the samples were immediately cooled at 2-8° C. prior to analyses for nalidixic acid resistant *Salmonella enteritidis* PT4.

The concentration of *Salmonella enteritidis* PT4 in digesta and spleen was determined after decimal dilutions of the samples in a buffered peptone solution. The diluted samples were inoculated on Brilliant Green Agar plates containing 100 µg/l nalidixic acid. Plates were incubated during 24 h at 37° C. Typical *Salmonella enteritidis* PT4 colonies were counted and the concentration of the *Salmonella enteritidis* PT4 (cfu/g) in the original samples was calculated according to standard procedures.

Growth Performance

All broilers were weighed per cage at 0, 15 and 30 days of age to determine the body weight (BW).

Feed intake (FI) was recorded per cage on day 15 and 24 of age.

Mortality per cage was recorded daily.

BW, body weight gain (BWG), FI, feed conversion ratio (FCR) and mortality were calculated over the following periods: 0-15 days, 15-30 days and the entire experimental period (0-30 days of age).

Animal Health Observations

Health of birds was checked daily and aberrations were recorded as well as probable cause of death for dead or culled birds. Temperature and humidity in the animal room were recorded.

Statistical Analyses

Growth Performance and Spleen Weight

Statistical analyses on growth performance and spleen weight data was performed within the "*Salmonella* challenged" treatments (treatment II-V). Response parameters were statistically analysed by ANOVA using GenStat statistical software (17th edition, VSN International Ltd., Hemel Hempstead, UK), using row/tier as block factor, and diet as explanatory variable according to the statistical model given below:

$$Y = \mu + \text{row}_i/\text{tier}_j + \text{diet}_k + e_{ijkl}$$

Where:

Y=Response parameter

µ=General mean row/tier=Row of battery cages (i=1,2) as block and within row tier (j=1,2,3) as sub-block diet=Effect of the diet (k=1 . . . 4)

e=Error term

The P-value of the treatment effect and the LSD (least significant difference (P=0.05)) were provided per response parameter. Treatment effects with a P-value≤0.05 were considered to be statistically significant.

*Salmonella enteritidis* PT4 Counts

To examine for differences in numbers (CFU/g) of *Salmonella* in the caecal digesta of chickens fed a diet containing 20, 28 or 36 mg/kg phenylcapsaicin compared to a control group on a diet without phenylcapsaicin. First a Pearson's chi-square test was performed on ranked (low to high) concentration values between the control and treatment group fed 20 mg/kg. Due to missing values, this analysis could not be done on the 28 and 36 mg/kg treatments. Since the broilers were kept in different cages, cages were first treated as random effect factors using a generalized linear mixed effects model (GLMM), applying the glmmPQL function from the MASS library of R, assuming Poisson distribution due to count data. Second, the data were analysed excluding the effect of cages by a generalized linear model applying the glm function from the MASS library of R, again assuming Poisson distribution. Analyses were performed on data from both sample days (day 20 and day 29; overall), and on data from day 20 and 29 separately. On day 20, the highest control value (1.3×CFU/g) and the two highest values in the 28 mg/kg treatment group (1.3×10' and 1.2×10$^7$ CFU/g) are considerable higher than the next highest value (1.1×10$^6$ and 4.0×10$^6$ CFU/g) for the control and 28 mg/kg treatment groups, respectively and were therefore considered to be outliers. Analysis were thus performed on the remaining data after excluding these data points.

Results

Spleen weight in *Salmonella* inoculated broilers at 20 and 29 d of age was numerically higher than spleen weight in broilers without *Salmonella* inoculation which implicates a successful *Salmonella* infection. Dietary supplementation of phenylcapsaicin at 20, 28 and 36 mg/kg did not affect the spleen weight at 20 and 29 days of age of the *Salmonella* inoculated broilers Broilers fed diets containing 20 mg/kg phenylcapsaicin numerically had lower *Salmonella* counts than control chickens on a diet without phenylcapsaicin (P values of 0.15 for both days (20 and 29 days of age) and 0.13 for day 29). The results are summarized in Table 3. The differences in ranked numbers are highly significant between the control and the 20 mg/kg treatment group, with the 20 mg/kg group having consistently lower *Salmonella* counts than the control group at both day 20 as well as day 29. The results are found in Table 4 and in FIG. 1. Caecal colonization of *Salmonella enteritidis* PT4 was not affected by dietary inclusion of 28 and 36 mg/kg phenylcapsaicin. These results implicate that most probably, the effective dose is in the range up to 20 mg/kg phenylcapsaicin instead of phenylcapsaicin dose levels over 20 mg/kg.

TABLE 3

Summary statistics from the generalized linear mixed model (where cage was treated as random effect factors using a generalized linear mixed effects model (GLMM), applying the glmmPQL function from the MASS library of R) and generalized linear model (without controlling for the random effect of cage, applying the glm function from the MASS library of R) used to examine for differences in CFU/g counts between chickens fed a diet containing 20 mg/kg phenylcapsaicin and chickens fed a control diets without phenylcapsaicin. Outliers are defined as values > $1.0 \times 10^7$ CFU/g.

| Input data | R test | Std. error | df | t value | P |
|---|---|---|---|---|---|
| Both days (day 20 and 29) | | | | | |
| All CFU/g counts | glmPQL | 3.521 | 106 | 0.223 | 0.82 |
| | glm | 3.521 | 116 | 0.229 | 0.82 |
| CFU/g counts; outliers masked | glmPQL | 1.507 | 105 | 1.469 | 0.15 |
| | glm | 1.507 | 115 | 1.469 | 0.15 |
| Day 20 | | | | | |
| All CFU/g counts | glmPQL | 1.444 | 10 | 1.240 | 0.24 |
| | glm | 1.444 | 58 | 1.240 | 0.22 |
| CFU/g counts; outliers masked | glmPQL | 0.468 | 10 | 0.822 | 0.43 |
| | glm | 0.468 | 57 | 0.822 | 0.41 |
| Day 29 | | | | | |
| All CFU/g counts | glmPQL | 1.580 | 10 | 1.646 | 0.13 |
| | glm | 1.580 | 58 | 1.646 | 0.11 |

TABLE 4

Summary statistics from the Pearson's chi-square test testing for differences in ranked numbers of *Salmonella* counts in caecal digesta

| Day | $\chi^2$ | df | Probability level |
|---|---|---|---|
| Day 20 | 21.6 | 1 | 0.001 |
| Day 29 | 6.67 | 1 | 0.01 |

In the *Salmonella* challenged birds, body weight (BW) and body weight gain (BWG) of broilers fed diets with 36 mg/kg of phenylcapsaicin was significantly lower than BW and BWG of broilers fed diets with 0, 20 or 28 mg/kg phenylcapsaicin. The lower body weight gain of broilers fed diets with 36 mg/kg resulted in a higher feed conversion ratio as compared to the other treatments with *Salmonella* inoculated broilers. Dietary inclusion of phenylcapsaicin had no effect on daily feed intake of *Salmonella* inoculated broilers.

In the grower phase (15-30 days), after *Salmonella* challenge, dietary inclusion of phenylcapsaicin at 20, 28 and 36 mg/kg did not affect feed intake and feed conversion ratio of *Salmonella* inoculated broilers. A tendency towards a lower BWG was observed by increasing the dose level of phenylcapsaicin (P=0.099). Broilers who received the diets with the highest phenylcapsaicin dose (36 mg/kg) had numerically the lowest BWG and the highest FCR.

Body weight (BW) and body weight gain (BWG) in *Salmonella* inoculated broilers fed diets with 36 mg/kg of phenylcapsaicin was significantly lower than BW and BWG in *Salmonella* inoculated broilers fed diets with 0, 20 or 28 mg/kg phenylcapsaicin. Dietary inclusion of phenylcapsaicin had no effect on daily feed intake and feed conversion ratio of *Salmonella* inoculated broilers Conclusion Dietary inclusion of 20 mg/kg phenylcapsaicin resulted in statistically significant differences in individually ranked caecal *Salmonella enteritidis* PT4 counts compared with the control treatment. This result can be an indicator of a *Salmonella* reducing effect of including 20 mg/kg phenylcapsaicin in broiler diets.

The invention claimed is:

1. A poultry feed comprising at least one chemical compound of the formula I:

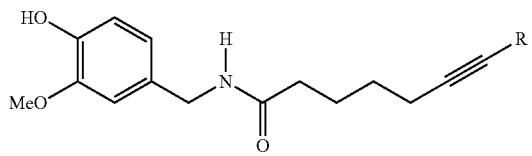

I wherein R is phenyl; or tautomers or salts thereof, and
wherein the feed comprises 5-20 mg/kg of the compound of formula I, or tautomer or salt thereof.

2. The poultry feed according to claim 1, wherein the feed is at least one feed selected from the group consisting of a seed, corn, a worm, a millet, an oat, and a peanut, and the feed is at least one form selected from the group consisting of a pellet, a slurry, drinking water, and an emulsion.

3. The poultry feed according to claim 1, wherein the poultry feed is selected from the group consisting of chicken feed, turkey feed, duck feed and goose feed.

4. The poultry feed according to claim 1, wherein the poultry feed is broiler chicken feed.

* * * * *